(12) United States Patent
Matsui et al.

(10) Patent No.: US 6,242,608 B1
(45) Date of Patent: Jun. 5, 2001

(54) 2-PHENYLPYRIDINE DERIVATIVE AND PRODUCTION METHOD THEREOF

(75) Inventors: Kozo Matsui; Kiyoshi Sugi; Yoshihide Umemoto; Tetsuya Shintaku; Nobushige Itaya, all of Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 09/602,031

(22) Filed: Jun. 23, 2000

Related U.S. Application Data

(62) Division of application No. 09/370,636, filed on Aug. 6, 1999, now Pat. No. 6,147,218.

(30) Foreign Application Priority Data

| Aug. 7, 1998 | (JP) | 10-224790 |
| Sep. 7, 1998 | (JP) | 10-252645 |
| Jul. 27, 1999 | (JP) | 11-212902 |

(51) Int. Cl.[7] .................................................. C07D 211/70
(52) U.S. Cl. ............................................................ 546/332
(58) Field of Search ............................................ 546/332

(56) References Cited

FOREIGN PATENT DOCUMENTS 0 972 765    1/2000   (EP).

Primary Examiner—Zinna Northington Davis
(74) Attorney, Agent, or Firm—Leydig, Voit & Mayer, Ltd.

(57) ABSTRACT

A series of compounds capable of deriving an intermediate for the production of a compound (A) of the following formula,

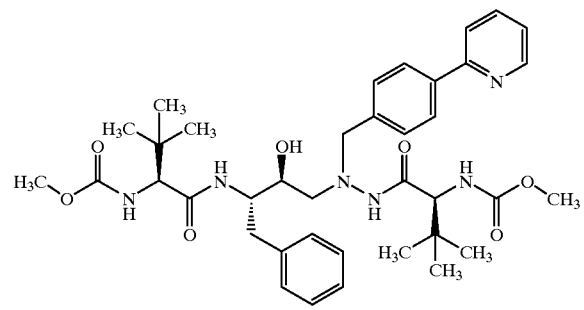

(A)

which is an anti-HIV drug, and a production method thereof. To be specific, 4-(pyridin-2-yl)benzaldehyde hydrazone, a production method of this compound, and a production method from this compound to N-(tert-butoxycarbonyl)-N'-[4-(pyridin-2-yl)phenylmethylidene]hydrazine. In addition, a salt of 2-(4-bromomethylphenyl)pyridine, 2-(4-dibromomethylphenyl)pyridine and a salt thereof, production methods of these compounds, and production methods to derive 4-(pyridin-2-yl)benzaldehyde which is a production intermediate for 4-(pyridin-2-yl)benzaldehyde hydrazone from these compounds.

2 Claims, No Drawings

2-PHENYLPYRIDINE DERIVATIVE AND PRODUCTION METHOD THEREOF

This is a divisional of application Ser. No. 09/370,636, filed on Aug. 6, 1999, now U.S. Pat. No. 6,147,218.

TECHNICAL FIELD OF THE INVENTION

The present invention relates to 4-(pyridin-2-yl) benzaldehyde hydrazone, a production method of this compound, and a method of producing N-(tert-butoxycarbonyl)-N'-[4-(pyridin-2-yl)phenylmethylidene] hydrazine from this compound. The present invention moreover relates to a salt of 2-(4-bromomethylphenyl)pyridine, 2-(4-dibromomethylphenyl)pyridine and a salt thereof, methods for the production of these compounds and a method of producing 4-(pyridin-2-yl)benzaldehyde, which is a production intermediate for 4-(pyridin-2-yl) benzaldehyde hydrazone, from these compounds. The above-mentioned hydrazine derivative is a compound useful as a production intermediate for compound (A) to be mentioned later, which is an anti-HIV drug.

BACKGROUND OF THE INVENTION

N-(tert-Butoxycarbonyl)-N'-[4-(pyridin-2-yl) phenylmethylidene]hydrazine in the present invention is useful as a synthetic intermediate for compound (A) represented by the following formula

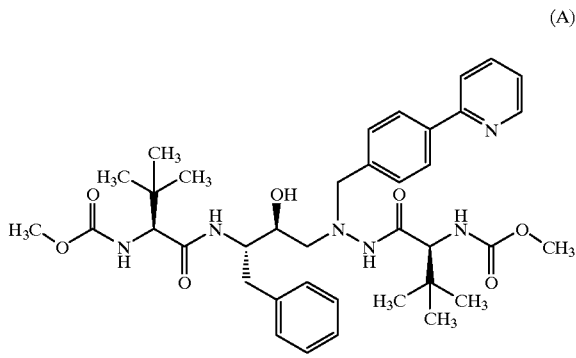

(A)

which is an anti-HIV drug, and the method for the production of the pharmaceutical compound (A) via the intermediate is described in, for example, WO97/40029.

WO97/40029 discloses a production method comprising reacting 4-(pyridin-2-yl)benzaldehyde with tert-butyl carbazate [tBuOC(=O)NHNH$_2$ wherein tBu is tert-butyl] to give N-(tert-butoxycarbonyl)-N'-[4-(pyridin-2-yl) phenylmethylidene]hydrazine, therefor 4-(pyridin-2-yl) benzaldehyde is important as an intermediate for a pharmaceutical product.

This method for the production of 4-(pyridin-2-yl) benzaldehyde includes a method disclosed in, for example, Japanese Patent Unexamined Publication No. 95157/1991 and WO97/40029, wherein Grignard reagent prepared from 4-bromobenzaldehyde dimethyl acetal and 2-bromopyridine are reacted using [1,3-bis(diphenylphosphino)propane] nickel(II) chloride as a catalyst. With regard to the above-mentioned production method, 4-bromobenzaldehyde dimethyl acetal and 2-bromopyridine, which are reaction reagents, are relatively expensive, and [1,3-bis (diphenylphosphino)propane]nickel(II) chloride, which is a catalyst, is extremely expensive and industrially hard to obtain. Thus, it is desired to have a method of producing 4-(pyridin-2-yl)benzaldehyde at a lower cost.

Inasmuch as tert-butyl carbazate used as the reagent in the aforementioned hydrazine derivative production method (WO97/40029) is expensive, a production method for producing N-(tert-butoxycarbonyl)-N'-[4-(pyridin-2-yl) phenylmethylidene]hydrazine industrially and economically has been awaited.

It is therefore an object of the present invention is to provide an economical method for the production of 4-(pyridin-2-yl)benzaldehyde, to provide an intermediate for producing 4-(pyridin-2-yl)benzaldehyde, and a method for the production of this intermediate. Another object of the present invention is to provide a method for producing N-(tert-butoxycarbonyl)-N'-[4-(pyridin-2-yl) phenylmethylidene]hydrazine economically and easily, as well as an intermediate (4-(pyridin-2-yl)benzaldehyde hydrazone) useful for producing this hydrazine derivative and a production method of this intermediate compound.

SUMMARY OF THE INVENTION

The present inventors have found that 4-(pyridin-2-yl) benzaldehyde can be produced economically by reacting a salt of 2-(4-bromomethylphenyl)pyridine, 2-(4-dibromomethylphenyl)pyridine or a salt thereof, all of which being novel compounds, with hexamethylenetetramine and water, and further that a salt of 2-(4-bromomethylphenyl) pyridine, 2-(4-dibromomethylphenyl)pyridine and a salt thereof can be obtained by reacting a salt of 2-(4-tolyl) pyridine with a brominating agent. In addition, they have found that N-(tert-butoxycarbonyl)-N'-[4-(pyridin-2-yl) phenylmethylidene]hydrazine can be produced more economically and easily by reacting 4-(pyridin-2-yl) benzaldehyde hydrazone with di-tert-butyl dicarbonate, and that 4-(pyridin-2-yl)benzaldehyde hydrazone can be obtained from 4-(pyridin-2-yl)benzaldehyde.

Accordingly, the present invention provides the following.

(1) 4-(Pyridin-2-yl)benzaldehyde hydrazone.
(2) A method for the production of N-(tert-butoxycarbonyl)-N'-[4-(pyridin-2-yl) phenylmethylidene]hydrazine of the formula (VI)

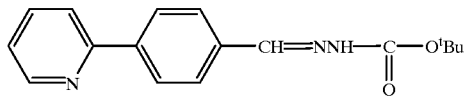

(VI)

wherein tBu is tert-butyl, comprising reacting 4-(pyridin-2-yl)benzaldehyde hydrazone of the formula (V)

(V)

with di-tert-butyl dicarbonate of the formula: [tBuOC(=O)]$_2$O wherein tBu is as defined above.

(3) The production method of the above-mentioned (2), wherein 4-(pyridin-2-yl)benzaldehyde hydrazone is obtained by reacting 4-(pyridin-2-yl)benzaldehyde of the formula (III)

with hydrazine.

(4) The production method of the above-mentioned (3), wherein 4-(pyridin-2-yl)benzaldehyde is obtained by reacting at least one member selected from the group consisting of a salt of 2-(4-bromomethylphenyl)pyridine of the formula (I)

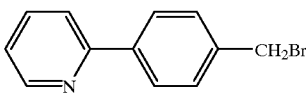
(I)

2-(4-dibromomethylphenyl)pyridine of the formula (II)

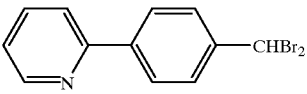
(II)

a salt thereof with hexamethylenetetramine and water.

(5) The production method of the above-mentioned (3), wherein 4-(pyridin-2-yl)benzaldehyde is obtained by reacting a salt of 2-(4-bromomethylphenyl)pyridine of the formula (I)

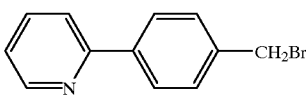
(I)

and/or a salt of 2-(4-dibromomethylphenyl)pyridine of the formula (II)

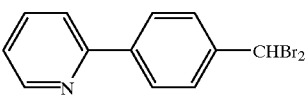
(II)

with hexamethylenetetramine and water.

(6) A method for the production of N-(tert-butoxycarbonyl)-N'-[4-pyridin-2-yl)phenylmethylidene]hydrazine comprising reacting at least one member selected from the group consisting of a salt of 2-(4-bromomethylphenyl)pyridine of the formula (I)

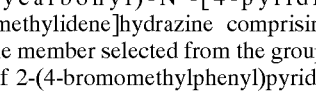
(I)

2-(4-dibromomethylphenyl)pyridine of the formula (II)

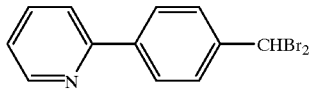
(II)

and a salt thereof, with hexamethylenetetramine and water to give 4-(pyridin-2-yl)benzaldehyde of the formula (III)

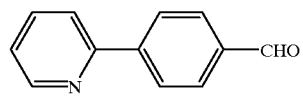
(III)

and reacting this compound with tert-butyl carbazate of the formula: tBuOC(=O)NHNH$_2$ wherein tBu is tert-butyl.

(7) The production method of the above-mentioned (6), wherein 4-(pyridin-2-yl)benzaldehyde is obtained by reacting a salt of 2-(4-bromomethylphenyl)pyridine of the formula (I)

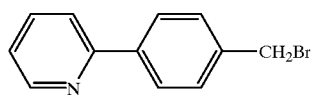
(I)

and/or a salt of 2-(4-dibromomethylphenyl)pyridine of the formula (II)

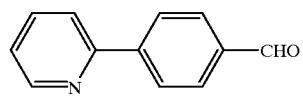
(II)

with hexamethylenetetramine and water.

(8) A method for the production of 4-(pyridin-2-yl)benzaldehyde hydrazone comprising reacting 4-(pyridin-2-yl)benzaldehyde with hydrazine.

(9) A method for the production of 4-(pyridin-2-yl)benzaldehyde of the formula (III)

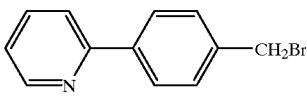
(III)

comprising reacting at least one member selected from the group consisting of a salt of 2-(4-bromomethylphenyl)pyridine of the formula (I)

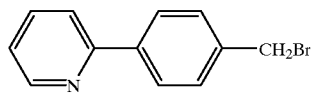
(I)

2-(4-dibromomethylphenyl)pyridine of the formula (II)

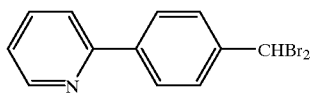
(II)

and a salt thereof, with hexamethylenetetramine and water.

(10) The production method of the above-mentioned (9), wherein the salt of 2-(4-bromomethylphenyl)pyridine of the formula (I)

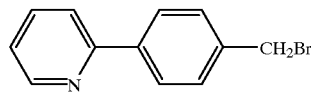
(I)

and/or the salt of 2-(4-dibromomethylphenyl)pyridine of the formula (II)

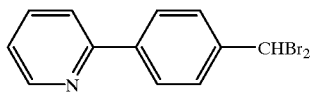
(II)

and hexamethylenetetramine and water are reacted.

(11) A salt of 2-(4-bromomethylphenyl)pyridine, 2-(4-dibromomethylphenyl)pyridine or a salt thereof.

(12) A method for the production of a salt of 2-(4-bromomethylphenyl)pyridine, 2-(4-dibromomethylphenyl)pyridine or a salt thereof, comprising reacting a salt of 2-(4-tolyl)pyridine of the formula (IV)

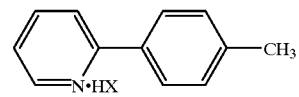
(IV)

wherein X is halogen atom or sulfonic acid residue, with a brominating agent.

(13) The production method of the above-mentioned (12), wherein X is halogen atom.

(14) The production method of the above-mentioned (12), wherein brominating agent is bromine.

In the production of a salt of 2-(4-bromomethylphenyl) pyridine, 2-(4-dibromomethylphenyl)pyridine, and a salt thereof, all of which are novel compounds, bromination of 2-(4-tolyl)pyridine without convertion into a salt results in an unintended product, because substituted benzyl bromide once generated reacts with the nitrogen atom in the molecule. The present inventors converted 2-(4-tolyl)pyridine into a salt and subjected the salt to bromination, whereby a salt of 2-(4-bromomethylphenyl)pyridine, 2-(4-bromomethylphenyl)pyridine, 2-(4-dibromomethylphenyl) pyridine, and a salt thereof were afforded without producing an unintended product.

EMBODIMENT OF THE INVENTION

The present invention is explained in detail in the following.

Production method of N-(tert-butoxycarbonyl)-N'-[4-(pyridin-2-yl)phenylmethylidene]hydrazine (VI)

N-(tert-Butoxycarbonyl)-N'-[4-(pyridin-2-yl) phenylmethylidene]hydrazine can be produced by, for example, ① reacting 4-(pyridin-2-yl)benzaldehyde with tert-butyl carbazate [tBuOC(=O)NHNH$_2$ where tBu is tert-butyl] (hereinafter also referred to as method ①) or ② reacting 4-(pyridin-2-yl)benzaldehyde hydrazone with di-tert-butyl dicarbonate [[tBuOC(=O)]$_2$O wherein tBu is as defined above] (hereinafter also referred to as method ②).

The production of N-(tert-butoxycarbonyl)-N'-[4-(pyridin-2-yl)phenylmethylidene]hydrazine by method ① follows the method disclosed in WO97/40029 or a method analogous thereto.

The production of N-(tert-butoxycarbonyl)-N'-[4-(pyridin-2-yl)phenylmethylidene]hydrazine by method ① comprises reaction of 4-(pyridin-2-yl)benzaldehyde with tert-butyl carbazate in the following solvent. More specifically, 4-(pyridin-2-yl)benzaldehyde is added to a solution of tert-butyl carbazate to give N-(tert-butoxycarbonyl)-N'-[4-pyridin-2-yl)phenylmethylidene] hydrazine. 4-(Pyridin-2-yl)benzaldehyde is preferably added to the reaction vessel as a solution of the following solvent.

The solvent to be used in this reaction includes, for example, methanol, ethanol, acetonitrile and tetrahydrofuran (THF), with preference given to methanol.

This solvent is preferably used in an amount of 2 to 10 times the amount in weight of 4-(pyridin-2-yl)benzaldehyde.

tert-Butyl carbazate is used in an amount of 1.0 to 3.0 times the molar amount of 4-(pyridin-2-yl)benzaldehyde, with preference given to 1.2 times the amount in mole thereof.

The reaction temperature is from ambient temperature to 70° C., preferably to 50° C.

The reaction time after adding the all reaction reagent is from 30 minutes to 20 hours, preferably to 2 hours.

The obtained N-(tert-butoxycarbonyl)-N'-[4-(pyridin-2-yl)phenylmethylidene]hydrazine can be isolated and purified by a known method such as washing, recrystallization and column chromatography.

The starting material, 4-(pyridin-2-yl)benzaldehyde, can be obtained by the production method to be mentioned later.

The method ② is explained in detail in the following.

The production of N-(tert-butoxycarbonyl)-N'-[4-pyridin-2-yl)phenylmethylidene]hydrazine by method ② comprises reacting 4-(pyridin-2-yl)benzaldehyde hydrazine with di-tert-butyl dicarbonate in the following solvent in the presence of an organic base or an inorganic base when necessary. The addition of an organic base or inorganic base to the reaction mixture accelerates the reaction. Di-tert-butyl dicarbonate is preferably added to the reaction mixture as a solution of the below-noted solvent. Inasmuch as di-tert-butyl dicarbonate (which is economical) is used in method ②, the hydrazone derivative can be produced more economically than in method ①.

The solvent to be used in this reaction is exemplified by tetrahydrofuran (THF), toluene, monochlorobenzene, water and a mixed solvent thereof, with preference given to THF and monochlorobenzene.

The solvent is used in an amount which is free of limitation as long as it facilitates stirring of the reaction mixture. For example, it is preferably used in 1 to 50 times, more preferably 1 to 10 times, the amount in weight of 4-(pyridin-2-yl)benzaldehyde hydrazone.

Di-tert-butyl dicarbonate is preferably used in an amount of 1 to 3 times, more preferably 1 to 1.5 times, the amount of mole of 4-(pyridin-2-yl)benzaldehyde hydrazone.

The organic base or inorganic base to be used in this reaction is added in a catalytic amount to 3 times the amount in mole of 4-(pyridin-2-yl)benzaldehyde hydrazone. The organic base is exemplified by tertiary amine such as trimethylamine and the inorganic base is exemplified by alkali metal hydroxide such as sodium hydroxide and potassium hydroxide, alkali metal carbonate such as sodium carbonate and potassium carbonate and alkali metal hydrogencarbonate such as sodium hydrogencarbonate and potassium hydrogencarbonate. Preferred is sodium hydroxide, which is generally used in the form of an aqueous solution.

The reaction temperature is from normal temperature to the boiling point of the solvent used, which is preferably from normal temperature to 60° C.

The reaction time after addition of all reaction reagents is from 30 minutes to 12 hours, preferably 1 to 3 hours, and more preferably 1 to 2 hours.

The obtained N-(tert-butoxycarbonyl)-N'-[4-(pyridin-2-yl)phenylmethylidene]hydrazine can be isolated and purified by a known method such as washing, recrystallization and column chromatography. For example, the reaction mixture is concentrated and washed for purification, and after washing, recrystallized from a suitable organic solvent (e.g., toluene) for further purification.

The starting material, 4-(pyridin-2-yl)benzaldehyde hydrazone, can be obtained by the production method to be mentioned later.

A method for the production of 4-(pyridin-2-yl)benzaldehyde hydrazone (V)

4-(Pyridin-2-yl)benzaldehyde hydrazone is a novel compound, and is useful as a synthetic intermediate for N-(tert-butoxycarbonyl)-N'-[4-(pyridin-2-yl)phenylmethylidene]hydrazine.

4-(Pyridin-2-yl)benzaldehyde hydrazone can be produced by reacting 4-(pyridin-2-yl)benzaldehyde with hydrazine. To be specific, hydrazine is mixed with lower alcohol and 4-(pyridin-2-yl)benzaldehyde is added thereto with stirring to allow reaction, or dropwise added in the form of an organic solvent solution with stirring to allow reaction. This reaction is preferably carried out in a homogeneous or near homogeneous system using hydrazine in excess of 4-(pyridin-2-yl)benzaldehyde.

Hydrazine is used in an amount of 1 to 5 times, preferably 1 to 3 times, the amount in mole of 4-(pyridin-2-yl) benzaldehyde. In the present invention, hydrazine to be used is preferably hydrazine hydrate from the economical and safety aspects.

The lower alcohol to be used in this reaction is alcohol having 1 to 3 carbon atoms, which is exemplified by methanol, ethanol, propanol, isopropanol and the like. The amount of the lower alcohol used is not particularly limited and is such an amount that makes the reaction mixture homogeneous or near homogeneous. For example, methanol is used in an amount of 1 to 10 times the amount in weight of 80% hydrazine hydrate.

The organic solvent in which 4-(pyridin-2-yl) benzaldehyde is dissolved is exemplified by the above-mentioned lower alcohol having 1 to 3 carbon atoms, ether solvent such as THF, aromatic solvent such as toluene, and halogenated hydrocarbon solvent such as monochlorobenzene, with preference given to lower alcohol. As the organic solvent, the solvent used for extraction in the previous step is preferably used to avoid complicated manipulation. The organic solvent is used in an amount of 0.5 to 20 parts by weight, preferably 3 to 10 parts by weight, per part by weight of 4-(pyridin-2-yl)benzaldehyde.

The reaction temperature is from ambient temperature to the boiling point of the solvent used, which is preferably from the ambient temperature to 50° C.

The reaction completes at the time of completion of dropwise addition of 4-(pyridin-2-yl)benzaldehyde or by incubation for about 3 hours after the dropwise addition. After the completion of the reaction, for example, the obtained reaction mixture containing 4-(pyridin-2-yl) benzaldehyde hydrazone is concentrated under reduced pressure, or, more specifically, lower alcohol is distilled off, followed by extraction to give the objective product solution. The solvent to be used for extraction includes ether solvent (e.g., tetrahydrofuran), halogenated aromatic solvent (e.g., monochlorobenzene), and the like. A small amount of alkali metal hydroxide (e.g., sodium hydroxide) is preferably added before concentration under reduced pressure or extraction, as a stabilizer of 4-(pyridin-2-yl)benzaldehyde hydrazone.

The starting material, 4-(pyridin-2-yl)benzaldehyde, can be obtained by the production method to be mentioned below.

A method for the production of 4-(pyridin-2-yl) benzaldehyde (III)

4-(Pyridin-2-yl)benzaldehyde is a known compound, and can be obtained by reacting a Grignard reagent prepared from, for example, 4-bromobenzaldehyde dimethyl acetal, with 2-bromopyridine in the presence of [1,3-bis (diphenylphosphino)propane]nickel(II) chloride and hydrolyzing the obtained 4-(pyridin-2-yl)benzaldehyde dimethyl acetal (Japanese Patent Unexamined Publication No. 95157/1991, WO97/40029). A new production method of this compound includes the following methods.

4-(Pyridin-2-yl)benzaldehyde can be obtained by reacting at least one of the compounds selected from the group of a salt of 2-(4-bromomethylphenyl)pyridine, 2-(4-dibromomethylphenyl)pyridine and a salt thereof, with hexamethylenetetramine and water. To be specific, water and hexamethylenetetramine are added to at least one of the compounds selected from the group of a salt of 2-(4-bromomethylphenyl)pyridine, 2-(4-dibromomethylphenyl) pyridine and a salt thereof in a reaction solvent, and the mixture is stirred with heating to give 4-(pyridin-2-yl) benzaldehyde. When necessary, a basic substance (e.g., sodium acetate) is added in an amount of 0.5–2.0 moles per mole of hexamethylenetetramine.

Water functions as a reaction reagent, as well as a solvent, wherein water as a reaction reagent is used in an amount of 2 to 10 times, preferably 4 to 6 times, the amount in weight of the starting compound of bromination, 2-(4-tolyl) pyridine, and water in excess by 10 times the amount in weight of 2-(4-tolyl)pyridine is used as a reaction solvent.

Usable reaction solvent other than water is ethanol, acetic acid and the like, preferably acetic acid. A single solvent such as water and a reaction solvent other than water, or a mixed solvent thereof can be used as a reaction solvent. A preferably mixed solvent is an aqueous acetic acid solution. The amount of the reaction solvent used is 2 to 10 times, preferably 4 to 7 times, the amount in weight of the starting material of bromination, 2-(4-tolyl)pyridine.

The amount of hexamethylenetetramine used as equimolar to 15 times, preferably 2 to 10 times, more preferably 3 to 10 times, the amount in mole of the starting material of bromination, 2-(4-tolyl)pyridine.

The reaction temperature is from ambient temperature to the boiling point of the solvent used, preferably 85–95° C.

The reaction time is 1 to 8 hours, preferably 1 to 3 hours.

4-(Pyridin-2-yl)benzaldehyde can be isolated by a conventional method such as extraction, distillation and column chromatography. For example, the acidic substance in the reaction mixture after reaction is neutralized, which is followed by extraction to give 4-(pyridin-2-yl)benzaldehyde. The compound can be also obtained as crystalline 4-(pyridin-2-yl)benzaldehyde alkali metal hydrogensulfite adduct by the use of hydrogensulfite species such as sodium hydrogensulfite or sodium pyrosulfite in water or a mixed solvent of water and lower alcohol or ethyl acetate. The obtained 4-(pyridin-2-yl)benzaldehyde alkali metal hydrogensulfite adduct is brought into contact with an acidic or alkaline aqueous solution to reproduce the original 4-(pyridin-2-yl)benzaldehyde. Utilizing this process, purification can be carried out.

As mentioned above, the method of the present invention does not involve the use of an expensive reaction reagent, so that 4-(pyridin-2-yl)benzaldehyde is provided economically. The starting material, a salt of 2-(4-bromomethylphenyl)pyridine (I), 2-(4-dibromomethylphenyl)pyridine (II) and a salt thereof can be obtained by the following production methods A method for the production of a salt of 2-(4-bromomethylphenyl)pyridine (I), 2-(4-dibromomethylphenyl)pyridine (II) and a salt thereof.

A salt of 2-(4-bromomethylphenyl)pyridine (hereinafter also referred to as a monobromo compound), 2-(4-dibromomethylphenyl)pyridine (hereinafter also referred to as a dibromo compound) and a salt thereof, all of which are starting compounds for the production of the above-mentioned 4-(pyridin-2-yl)benzaldehyde, are novel compounds and can be obtained by reacting a salt of 2-(4-tolyl)pyridine with a brominating agent. To be specific, for example, a brominating agent is added to a mixture of a salt of 2-(4-tolyl)pyridine and a solvent with heating to give a salt of the monobromo compound and a salt of the dibromo compound, and, if necessary, the salt of the dibromo compound can be processed appropriately to give a dibromo compound in the form of a free base. The salt of monobromo compound and the salt of dibromo compound can be separated by a purification means such as recrystallization. It is also possible to separate into a monobromo compound and a dibromo compound by converting a mixture of the salt of monobromo compound and the salt of dibromo compound into free base mixture and subjecting the free base mixture to purification by column chromatography and the like. When a brominating agent is used in a large amount, the monobromo compound is converted to a dibromo compound, so that the proportion of the dibromo compound in the product becomes high. When necessary, hydrobromic acid generated in the reaction mixture can be removed by introducing a nitrogen gas. A salt of 2-(4-tolyl)pyridine may be formed before bromination or concurrently with bromination in the same reaction mixture.

The salt of monobromo compound and the salt of dibromo compound are exemplified by hydrochloride, hydrobromide, sulfate, benzenesulfonate, methanesulonate, p-toluenesulfonate and the like.

In the formula (IV), X is halogen atom or sulfonic acid residue. The halogen atom is preferably chlorine or bromine and the sulfonic acid residue is preferably exemplified by residues of sulfuric acid, benzenesulfonic acid, methanesulfonic acid, p-toluenesulfonic acid and the like. More preferred X is chlorine or benzenesulfonic acid residue.

The method of forming a salt of 2-(4-tolyl)pyridine is not particularly limited. When it is prepared before bromination, for example, an inorganic acid or organic acid is added in various forms to a solution of 2-(4-tolyl)pyridine. The reaction solvent thereof is exemplified by lower alcohol having 1 to 3 carbon atoms, such as methanol, ethanol, propanol, isopropanol and the like, and halogenated hydrocarbon solvent such as chlorobenzene, with preference given to chlorobenzene.

The amount of the reaction solvent to be used is 1 to 6 times, preferably 3 to 4 times, the amount in weight of 2-(4-tolyl)pyridine.

The inorganic acid to be used for forming a salt of 2-(4-tolyl)pyridine is free of particular limitation and is preferably hydrochloric acid or hydrobromic acid.

The organic acid to be used for forming a salt of 2-(4-tolyl)pyridine is exemplified by benzenesulfonic acid, methanesulfonic acid, p-toluenesulfonic acid and the like, preferably benzenesulfonic acid. These organic acids may be in the form of hydrate or aqueous solution.

The amount of the inorganic acid and organic acid to be used is 0.5 to 1.5 times, preferably 1.0 to 1.1 times, the amount in mole of 2-(4-tolyl)pyridine.

When the salt of 2-(4-tolyl)pyridine is prepared in the same reaction vessel for bromination, 2-(4-tolyl)pyridine hydrobromide can be obtained by reacting hydrobromic acid generated during bromination of 2-(4-tolyl)pyridine.

The bromination reaction of the salt of 2-(4-tolyl)pyridine mentioned above is explained in the following.

The brominating agent to be used for the bromination reaction is exemplified by bromine, 1,3-dibromo-5,5-dimethylhydrantoin, N-bromosuccinimide and the like, preferably bromine.

The amount of the brominating agent to be used is 1.0 to 3.0 times, preferably 1.3 to 2.3 times, more preferably 1.4 to 2.3 times, the amount in mole of 2-(4-tolyl)pyridine.

The reaction solvent in the bromination reaction is preferably an inert solvent, which is specifically chlorobenzene, o-dichlorobenzene, 1,2-dichloroethane and the like, with preference given to chlorobenzene.

The amount of the reaction solvent to be used is not particularly limited, but it is preferably 0.2–1.0 L per mole of 2-(4-tolyl)pyridine.

The reaction temperature of bromination reaction is from ambient temperature to the boiling point of the solvent used, preferably 100–130° C.

The reaction time of bromination reaction is 6 to 18 hours, preferably 10 to 14 hours.

The monobromo compound and the dibromo compound obtained after the reaction are in the form of salts. When the reaction mixture is neutralized and isolated by a conventional method, such as extraction and column chromatography, a monobromo compound and a dibromo compound that are not in the form of salts can be obtained. When the monobromo compound and the dibromo compound are used for the synthesis of 4-(pyridin-2-yl)benzaldehyde, they can be used in the form of salts. In this way, neutralization and isolation can be omitted, and the use of salts of the monobromo compound and dibromo compound is preferable. When the salt(s) of the monobromo compound and/or the dibromo compound are/is used for the synthesis of 4-(pyridin-2-yl)benzaldehyde, the reaction mixture can be used in the next step without removing the solvent therefrom.

The method for the production of 2-(4-tolyl)pyridine, which is the starting material of the present invention, is disclosed in Tetrahedron, 54, 1289–1298 (1998) and the like. For example, tolylzinc halide obtained electrochemically is reacted with 2-halopyridine using a nickel catalyst to give 2-(4-tolyl)pyridine.

N-(tert-Butoxycarbonyl)-N'-[4-(pyridin-2-yl) phenylmethylidene]hydrazine obtained by the method of the present invention is useful as a synthetic intermediate for the aforementioned compound (A) (anti-HIV drug) and can be converted into an anti-HIV drug (A) by the method disclosed in WO97/40029.

The present invention is explained in detail by illustrative examples, to which the present invention is not limited in any way.

EXAMPLE 1

Production of 2-(4-bromomethylphenyl)pyridine Hydrochloride

In a 100 ml four neck flask were placed 2-(4-tolyl) pyridine hydrochloride (5.0 g, 24.3 mmol) and chlorobenzene (15 ml), and bromine (8.5 g, 53.2 mmol) was added dropwise over 12 hours while heating the mixture to 110–120° C. The mixture was stirred with heating at a temperature in the above-mentioned range for 1 hour. The reaction mixture was analyzed by high performance liquid chromatography (hereinafter abbreviated as HPLC). As a result, 2-(4-bromomethylphenyl)pyridine was confirmed to have been produced in a 64.5% yield. The reaction mixture was cooled to allow precipitation of the crystals, which were collected by filtration and washed with a small amount of cold methanol. From the $^1$H-NMR analysis, the compound was found to be 2-(4-bromomethylphenyl)pyridine hydrochloride.

[2-(4-bromomethylphenyl)pyridine hydrochloride]
$^1$H-NMR (DMSO-$d_6$, ppm) δ: 4.83 (s,2H), 7.73(d,J=8.0 Hz,2H), 7.94–8.02 (m,2H), 8.05(d,J=8.0 Hz,2H), 8.38–8.45 (m,1H), 8.54–8.58(m,1H), 8.91 (d,J=5.2 Hz,1H)

EXAMPLE 2

Production of 4-(pyridin-2-yl)benzaldehyde

To a reaction vessel containing 2-(4-bromomethylphenyl) pyridine hydrochloride obtained in Example 1 was added a mixed solution of hexamethylenetetramine (25.5 g, 181.9 mmol) dissolved in a mixed solvent of acetic acid (25 ml) and deionized water (25 ml) at room temperature. Then, the mixture was stirred with heating at a temperature in the range of 80–90° C. for 1 hour.

The reaction mixture was analyzed by HPLC. As a result, 4-(pyridin-2-yl)benzaldehyde was confirmed to have been produced in a 79.9% yield. The reaction mixture containing 4-(pyridin-2-yl)benzaldehyde was neutralized by adding 10M aqueous sodium hydroxide solution (35 ml). The resulting solution was extracted with toluene (40 ml) and the solvent was evaporated under reduced pressure. The obtained solution was used for the next reaction.

EXAMPLE 3

Production of 4-(pyridin-2-yl)benzaldehyde Hydrazone

To a mixture of 80% hydrazine hydrate (1.64 g, 26.2 mmol) and methanol (5.0 ml) was dropwise added a solution of 4-(pyridin-2-yl)benzaldehyde (1.5 g, 8.2 mmol) in methanol (5.0 ml) at 25° C. over 10 minutes. After the dropwise addition, the mixture was stirred for 30 minutes. Methanol and excess hydrazine hydrate were evaporated under reduced pressure. The residue was crystallized and 4-(pyridin-2-yl)benzaldehyde hydrazine was obtained as crude crystals at a yield of 1.6 g (yield:100%). The percentage of the area of 4-(pyridin-2-yl)benzaldehyde hydrazone in the crude crystals as determined by liquid chromatography was 94.3%.

crude crystals melting point: 65.7–67.8° C.

IR(KBr)cm$^{-1}$: 3700–3000, 1636, 1590, 1468, 1432, 1394, 1150, 1114, 924, 840, 778, 742, 726.

$^1$H-NMR(CDCl$_3$) δ:5.60(s,2H), 7.22(m,1H), 7.65(d,2H), 7.74(m,2H), 7.78(s,1H), 8.00(d,2H), 8.69(d,1H)

EXAMPLE 4

Production of 4-(pyridin-2-yl)benzaldehyde Hydrazone

In a 100 ml four neck flask were placed 80% hydrazine hydrate (1.5 g, 24.0 mmol) and methanol (5 ml), and a solution of 4-(pyridin-2-yl)benzaldehyde (2.19 g, 12.0 mmol) obtained in Example 2 in methanol (5 ml) was added dropwise over 1 hour at 25° C. with stirring. The mixture was stirred at 25° C. for 1 hour and analyzed by HPLC. As a result, 4-(pyridin-2-yl)benzaldehyde hydrazone was confirmed to have been produced in a 85.1% yield. After the completion of the reaction, 1.0M aqueous sodium hydroxide solution (30 ml) was added to the reaction mixture and methanol was evaporated by a rotary evaporator. The precipitated crude crystals were partially taken out, dried and subjected to $^1$H-NMR analysis to confirm 4-(pyridin-2-yl) benzaldehyde hydrazone. To the residue was added THF (60 ml) and the mixture was extracted and used in Example 6.

crude crystals melting point: 65.7–67.8° C.

IR(KBr)cm$^{-1}$: 3700–3000, 1636, 1590, 1468, 1432, 1394, 1150, 1114, 924, 840, 778, 742, 726

$^1$H-NMR(CDCl$_3$, ppm) δ:5.60(s,2H), 7.22(m,1H), 7.65(d, 2H), 7.74(m,2H), 7.78(s,1H), 8.00(d,2H), 8.69(d,1H)

EXAMPLE 5

Production of N-(tert-butoxycarbonyl)-N'-[4-(pyridin-2-yl)phenylmethylidene]hydrazine 4-(Pyridin-2-yl)benzaldehyde hydrazone (1.6 g, 8.1 mmol) obtained in Example 3 was dissolved in tetrahydrofuran (5 g) and 40% aqueous sodium hydroxide solution (0.1 g) was added. Thereto was added dropwise a solution of di-tert-butyl dicarbonate (1.77 g, 8.1 mmol) in tetrahydrofuran (1 ml) at room temperature over 10 minutes. The mixture was stirred at 55–60° C. for 1 hour. The percentage of the area of the objective product after reaction as determined by liquid chromatography was 93.7%. The crystalline residue after concentration was washed and purified with a small amount of methanol to give N-(tert-butoxycarbonyl)-N'-[4-(pyridin-2-yl)phenylmethylidene]hydrazine (2.1 g, yield: 87%). The obtained crystals were used for the analysis after purification by recrystallization from toluene. The percentage of the area of N-(tert-butoxycarbonyl)-N'-[4-(pyridin-2-yl)phenylmethylidene]hydrazine contained at this stage as determined by liquid chromatography was 99.3%. Various spectrum data of N-(tert-butoxycarbonyl)-N'-[4-(pyridin-2-yl)phenylmethylidene]hydrazine after recrystallization are shown in the following.

melting point: 169.2~171.5° C.

IR(KBr)cm$^{-1}$: 3308, 1712, 1612, 1586, 1528, 1510, 1468, 1434, 1394, 1360, 1310, 1246, 1158, 780.

$^1$H-NMR(CDCl$_3$) δ: 1.55(s,9H), 7.24(m,1H), 7.75(m, 2H), 7.78(d,2H), 7.87(s,1H), 8.00(d,2H), 8.16(s,1H), 8.70 (m,1H)

EXAMPLE 6

Production of N-(tert-butoxycarbonyl)-N'-[4-(pyridin-2-yl)phenylmethylidene]hydrazine In a 100 ml four neck flask were placed 4-(pyridin-2-yl) benzaldehyde hydrazone (2.2 g, 12.0 mmol) obtained in Example 4, THF (50 ml) and 0.5M aqueous sodium hydroxide solution (10 ml), and a solution of di-tert-butyl dicarbonate (5.2 g, 23.8 mmol) in THF (5 ml) was added dropwise at 30° C. over 20 minutes with stirring. The mixture was heated to 55–60° C. and vigorously stirred for 3 hours. The reaction mixture was analyzed by HPLC. As a result, N-(tert-butoxycarbonyl)-N'-[4-(pyridin-2-yl) phenylmethylidene]hydrazine was confirmed to have been produced in a 93.2% yield. The reaction mixture was concentrated under reduced pressure, and the crystalline residue was washed with a small amount of cold methanol and recrystallized from toluene to give N-(tert-butoxycarbonyl)-N'-[4-(pyridin-2-yl)phenylmethylidene]hydrazine (yield 2.1 g). Various spectrum data of the obtained N-(tert-butoxycarbonyl)-N'-[4-(pyridin-2-yl)phenylmethylidene] hydrazine are shown in the following.

melting point: 169.2–171.5° C.

IR(KBr)cm$^{-1}$: 3308, 1712, 1612, 1586, 1528, 1510, 1468, 1434, 1394, 1360, 1310, 1246, 1158, 780

$^1$H-NMR(CDCl$_3$, ppm) δ: 1.55(s,9H), 7.24(m,1H), 7.75 (m,2H), 7.78(d,2H), 7.87(s,1H), 8.00(d,2H), 8.16(s,1H), 8.70(m,1H)

EXAMPLE 7

Production of N-(tert-butoxycarbonyl)-N'-[4-(pyridin-2-yl)phenylmethylidene]hydrazine In a 100 ml four neck flask were placed tert-butyl carbazate (1.87 g, 14.1 mmol) and methanol (5 ml), and a solution of 4-(pyridin-2-yl)benzaldehyde (2.16 g, 11.8 mmol) obtained in Example 2 in methanol (5 ml) was added dropwise at 25° C. over 20 minutes with stirring. The reaction mixture was stirred at 50° C. for 2 hours and analyzed by HPLC. As a result, N-(tert-butoxycarbonyl)-N'-[4-(pyridin-2-yl)phenylmethlidene]hydrazine was confirmed to have been produced quantitatively. The reaction mixture was concentrated under reduced pressure, and the crystalline residue was washed with a small amount of cold methanol to give N-(tert-butoxycarbonyl)-N'-[4-(pyridin-2-yl)phenylmethylidene]hydrazine (yield 2.3 g). Various spectrum data of the obtained N-(tert-butoxycarbonyl)-N'-[4-(pyridin-2-yl)phenylmethylidene]hydrazine were the same as those obtained in Example 6.

EXAMPLE 8

Production of 2-(4-dibromomethylphenyl)pyridine

In a 100 ml four neck flask were placed 2-(4-tolyl) pyridine (5.0 g, 29.6 mmol) and chlorobenzene (18 ml), and bromine (9.4 g, 59.1 mmol) was added dropwise while heating the mixture at 110–120° C. over 12 hours. The reaction mixture was stirred with heating at a temperature in the above-mentioned range for 1 hour and analyzed by HPLC. As a result, 2-(4-bromomethylphenyl)pyridine was confirmed to have been produced in a 60.7% yield. The obtained reaction mixture was cooled and the precipitated 2-(4-bromomethylphenyl)pyridine salt was collected by filtration. The filtrate was neutralized with 5% aqueous sodium hydroxide solution. After washing with water, the mixture was dried over anhydrous magnesium sulfate. Chlorobenzene was evaporated under reduced pressure and the residue was subjected to silica gel column chromatography (eluent: ethyl acetate-hexane) to give 2-(4-dibromomethylphenyl) pyridine in a 1.2 g yield. From the $^1$H-NMR analysis, the product was found to be 2-(4-dibromomethylphenyl) pyridine.

[2-(4-dibromomethylphenyl)pyridine]

$^1$H-NMR(CDCl$_3$, ppm) δ: 6.70(s,1H), 7.23–7.29(m,1H), 7.66–7.68 (d,2H), 7.68–7.78 (m,2H), 7.98–8.01(d,2H), 8.69–8.71 (m,1H).

EXAMPLE 9

Production of 4-(pyridin-2-yl)benzaldehyde 2-(4-Dibromomethylphenyl)pyridine (100 mg, 0.306 mmol) obtained in Example 8 was placed in a 30 ml four neck flask and dissolved in chlorobenzene (0.1 ml). Hexamethylenetetramine (192 mg, 1.37 mmol) was dissolved in a mixed solvent of acetic acid (0.2 ml) and deionized water (0.2 ml) at room temperature and the solution was added. The mixture was stirred at 80° C. for 1 hour with heating. Then, the reaction mixture was analyzed by HPLC to confirm production of 4-(pyridin-2-yl)benzaldehyde. The percentage of the area of 4-(pyridin-2-yl)benzaldehyde in the reaction mixture after removing the solvent as determined by liquid chromatography was 60.0%.

EXAMPLE 10

Production of 4-(pyridin-2-yl)benzaldehyde

A reaction mixture (corresponding to 8.9 mmol) containing 2-(4-bromomethylphenyl)pyridine salt and 2-(4-dibromomethylphenyl)pyridine salt, both obtained in Example 8, was placed in a 50 ml flask and suspended in chlorobenzene (5 ml). Hexamethylenetetramine (6.4 g, 45.8 mmol) was dissolved in a mixed solvent of acetic acid (6 ml) and deionized water (6 ml) at room temperature and the solution was added. The mixture was stirred at 80° C. for 1 hour with heating. Then, the reaction mixture was analyzed by HPLC to confirm production of 4-(pyridin-2-yl) benzaldehyde. The percentage of the area of 4-(pyridin-2-yl)benzaldehyde in the reaction mixture after removing the solvent as determined by liquid chromatography was 70.0%.

EXAMPLE 11

Production of 2-(4-bromomethylphenyl)pyridine Benzenesulfonate and 2-(4-dibromomethylphenyl) pyridine Benzenesulfonate In a 300 ml four neck flask equipped with a water separator were placed 2-(4-tolyl)pyridine (20.0 g, 0.118 mol), chlorobenzene (100 ml) and benzenesulfonic acid monohydrate (20.82 g, 0.118 mol), and the mixture was heated. At around 90° C., water was azeotropically distilled into the water separator. The mixture was further heated while distilling water until the temperature of the distillate reached 131° C. Bromine (26.4 g, 0.165 mol) was added dropwise to this reaction mass at 120–130° C. over 8 hours.

The reaction mixture was stirred with heating at a temperature in the above-mentioned range for 4 hours and analyzed by HPLC. As a result, 2-(4-bromomethylphenyl)pyridine was confirmed to have been produced in a 68.89% yield and 2-(4-dibromomethylphenyl)pyridine was confirmed to have been produced in a 19.49% yield. This reaction mass was used as it was in the next reaction. From the $^1$H-NMR analysis, production of 2-(4-bromomethylphenyl)pyridine benzenesulfonate and 2-(4-dibromomethylphenyl)pyridine benzenesulfonate was confirmed.

[2-(4-bromomethylphenyl)pyridine benzenesulfonate]

$^1$H-NMR (CDCl$_3$, ppm) δ: 4.575(s,2H), 7.03–7.05 (m,1H), 7.35–7.42(m,3H), 7.63(d,J=8 Hz,2H), 7.80–7.87(m, 2H), 7.88–8.05(m,1H), 7.99(d,J=8 Hz,2H), 8.21–8.24(m, 1H), 8.50–8.56(m,1H)

[2-(4-dibromomethylphenyl)pyridine benzenesulfonate]

$^1$H-NMR(CDCl$_3$, ppm) δ: 6.886(s,1H), 7.03–7.05(m,1H), 7.35–7.42(m,3H), 7.63(d,J=8 Hz,2H), 7.8–8.07(m,1H), 7.88–8.07(m,1H), 7.99(d,J=8 Hz,2H), 8.21–8.24(m,1H), 8.49–8.6(m,1H)

EXAMPLE 12

Production of 4-(pyridin-2-yl)benzaldehyde

To a reaction vessel containing 2-(4-bromomethylphenyl) pyridine benzenesulfonate and 2-(4-dibromomethylphenyl) pyridine benzenesulfonate obtained in Example 11 was added a mixed solution of hexamethylenetetramine (33.08 g, 0.236 mol), sodium acetate (19.36 g, 0.236 mol) and deionized water (80 ml) at room temperature. The mixture was stirred with heating at 90–95° C. for 3 hours. After the completion of the reaction, the reaction mixture was neutralized with 20% aqueous sodium hydroxide solution (50 g) and the chlorobenzene layer was analyzed by HPLC to confirm production of 4-(pyridin-2-yl)benzaldehyde in a 81.8% yield.

According to the present invention, 4-(pyridin-2-yl) benzaldehyde, which is a synthetic intermediate for N-(tert-butoxycarbonyl)-N'-[4-(pyridin-2-yl)phenylmethylidene] hydrazine, can be produced economically via a salt of 2-(4-bromomethylphenyl)pyridine, 2-(4-dibromomethylphenyl)pyridine, or a salt thereof, all of which are novel compounds. According to the present invention, moreover, N-(tert-butoxycarbonyl)-N'-[4-(pyridin-2-yl)phenylmethylidene]hydrazine can be produced industrially and economically using a novel compound, 4-(pyridin-2-yl)benzaldehyde hydrazone, obtained by reacting 4-(pyridin-2-yl)benzaldehyde and hydrazine. The obtained N-(tert-butoxycarbonyl)-N'-[4-(pyridin-2-yl)phenylmethylidene]hydrazine can be used by the method described in, for example, WO97/40029 to give a pharmaceutical compound (A), thereby providing an anti-HIV drug economically and easily.

This application is based on patent application Nos. 252645/1998, 224790/1998 and 212902/1999 filed in Japan, the contents of which are hereby incorporated by reference.

What is claimed is:

1. 4-(Pyridin-2-yl)benzaldehyde hydrazone.

2. A method for the production of 4-(pyridin-2-yl) benzaldehyde hydrazone comprising reacting 4-(pyridin-2-yl)benzaldehyde with hydrazine.

* * * * *

UNITED STATES PATENT AND TRADEMARK OFFICE
CERTIFICATE OF CORRECTION

PATENT NO. : 6,242,608 B1
DATED : June 5, 2001
INVENTOR(S) : Matsui et al.

It is certified that error appears in the above-identified patent and that said Letters Patent is hereby corrected as shown below:

Title page,
Under "References Cited," the following citations are added:

FOREIGN PATENT DOCUMENTS:
WO 97/40029        10/1997        (WO).

OTHER PUBLICATIONS:
Chemical Abstracts of Japan, Vol. 131, No. 115, 92267 (JP-A-03-95157) (Jun. 1, 1989)

Chemical Abstracts, Vol. 80, No. 23, 133263m (XP-002121932) (1974)

Chemical Abstracts, Vol. 82, No. 23, 156085k (XP-002121933) (1975)

Signed and Sealed this

Eighteenth Day of December, 2001

Attest:

JAMES E. ROGAN
Attesting Officer    Director of the United States Patent and Trademark Office